United States Patent
Bar-Or et al.

(10) Patent No.: US 11,129,878 B1
(45) Date of Patent: Sep. 28, 2021

(54) METHODS FOR TREATING DISEASES ASSOCIATED WITH RESPIRATORY VIRUSES

(71) Applicant: Ampio Pharmaceuticals, Inc., Englewood, CO (US)

(72) Inventors: David Bar-Or, Englewood, CO (US); Holli Cherevka, Highlands Ranch, CO (US)

(73) Assignee: AMPIO PHARMACEUTICALS, INC., Englewood, CO (US)

(*) Notice: Subject to any disclaimer, the term of this patent is extended or adjusted under 35 U.S.C. 154(b) by 0 days.

(21) Appl. No.: 17/211,553

(22) Filed: Mar. 24, 2021

Related U.S. Application Data

(60) Provisional application No. 62/994,171, filed on Mar. 24, 2020.

(51) Int. Cl.
| | |
|---|---|
| *A61K 38/38* | (2006.01) |
| *A61K 9/00* | (2006.01) |
| *A61K 31/495* | (2006.01) |
| *A61P 31/14* | (2006.01) |
| *A61K 31/20* | (2006.01) |
| *A61P 11/00* | (2006.01) |
| *A61K 31/405* | (2006.01) |

(52) U.S. Cl.
CPC .......... *A61K 38/385* (2013.01); *A61K 9/0078* (2013.01); *A61K 31/20* (2013.01); *A61K 31/405* (2013.01); *A61K 31/495* (2013.01); *A61P 11/00* (2018.01); *A61P 31/14* (2018.01)

(58) Field of Classification Search
CPC .. A61K 38/385; A61K 9/0078; A61K 31/405; A61K 31/20; A61K 31/495; A61P 11/00; A61P 31/14
See application file for complete search history.

(56) References Cited

U.S. PATENT DOCUMENTS

| | | | |
|---|---|---|---|
| 4,289,759 A | 9/1981 | Heavner et al. | |
| 4,331,595 A | 5/1982 | Heavner et al. | |
| 4,694,081 A | 9/1987 | Miller et al. | |
| 4,940,709 A | 7/1990 | Shimazaki et al. | |
| 5,700,804 A | 12/1997 | Collins et al. | |
| 5,750,530 A | 5/1998 | Bryans et al. | |
| 5,817,751 A | 10/1998 | Szardenings et al. | |
| 5,932,579 A | 8/1999 | Campbell et al. | |
| 5,990,112 A | 11/1999 | Campbell et al. | |
| 6,555,543 B2 | 4/2003 | Bar-Or et al. | |
| 7,732,403 B2 | 6/2010 | Bar-Or et al. | |
| 9,005,665 B2* | 4/2015 | Gourapura | A61K 39/39 424/489 |
| 9,457,074 B2* | 10/2016 | Gourapura | A61K 39/12 |
| 9,714,283 B2* | 7/2017 | Grossman | A61K 45/06 |
| 9,815,886 B2* | 11/2017 | Grossman | A61P 31/04 |
| 9,956,217 B2 | 5/2018 | Bar-Or | |
| 9,969,793 B2* | 5/2018 | Grossman | A61P 31/12 |
| 10,279,028 B2* | 5/2019 | Gourapura | A61K 39/385 |
| 10,683,343 B2* | 6/2020 | Grossman | A61P 31/12 |
| 10,925,889 B2* | 2/2021 | Peyman | A61F 9/0017 |
| 2004/0024180 A1 | 2/2004 | Drauz et al. | |
| 2012/0058934 A1 | 3/2012 | Bar-Or | |
| 2014/0294738 A1 | 10/2014 | Bar-Or | |
| 2016/0367644 A1* | 12/2016 | Bar-Or | A61P 19/02 |
| 2019/0240296 A1 | 8/2019 | Bar-Or et al. | |
| 2020/0035474 A1* | 1/2020 | Nishiguchi | H01J 49/4215 |
| 2020/0384034 A1* | 12/2020 | Glassberg Csete | A61K 35/17 |
| 2021/0008105 A1* | 1/2021 | Martin | A61K 9/0073 |
| 2021/0070883 A1* | 3/2021 | Garcia | A61P 35/00 |

FOREIGN PATENT DOCUMENTS

| | | |
|---|---|---|
| EP | 0043219 | 1/1982 |
| JP | S63-290868 | 11/1988 |
| JP | 3176478 | 7/1991 |
| WO | WO 96/00391 | 1/1996 |
| WO | WO 97/36888 | 10/1997 |
| WO | WO 97/48685 | 12/1997 |
| WO | WO 99/40931 | 8/1999 |
| WO | WO 2009/039854 | 4/2009 |

OTHER PUBLICATIONS

Holshue et al. First Case of 2019 Novel Coronavirus in the United States. The New England Journal of Medicine. 382, vol. 10, pp. 929-936. First Published Jan. 31, 2020. (Year: 2020).*
Huang et al. Clinical features of patients infected with 2019 novel coronavirus in Wuhan, China. Lancet, vol. 395, Published Online Jan. 24, 2020. pp. 497-506. (Year: 2020).*
Alvarez et al., "Isolation and Structure Elucidation of Two New Calpain Inhibitors From Streptomyces griseus", The Journal of Antibiotics, 1994, vol. 47, Iss. 11, pp. 1195-1201.
American Thoracic Society, "ATS statement: Guidelines for the six-minute walk test", American Journal of Respiratory and Critical Care Medicine, 2002, vol. 166, Iss. 1, pp. 111-117.
Bar-Or et al., "On the Mechanisms of Action of the Low Molecular Weight Fraction of Commercial Human Serum Albumin in Osteoarthritis", Current Rheumatology Reviews, 2019, vol. 15, Iss. 3, pp. 189-200.
Borg, "Psychophysical bases of perceived exertion", Medicine & Science in Sports & Exercise, 1982; vol. 14, No. 5, pp. 377-381.
Fukunaga et. al., "Cyclooxygenase 2 Plays a Pivotal Role in the Resolution of Acute Lung Injury", The Journal of Immunology, 2005, vol. 174, Iss. 8, pp. 5033-5039.

(Continued)

*Primary Examiner* — Marcela M Cordero Garcia
(74) *Attorney, Agent, or Firm* — Sheridan Ross P.C.

(57) ABSTRACT

The present disclosure provides a method of treating a disease associated with a respiratory virus. The method comprises administering an effective amount of a pharmaceutical composition prepared by removing albumin from a solution of a human serum albumin composition and/or comprising a diketopiperazine with amino acid side chains of aspartic acid and alanine (DA-DKP), such as a low molecular weight fraction of human serum albumin. The present disclosure also provides a pharmaceutical product as well as a kit comprising DA-DKP.

18 Claims, No Drawings

(56) References Cited

OTHER PUBLICATIONS

Gao et al., "Resolvin D1 Improves the Resolution of Inflammation via Activating NF-κB p50/p50-Mediated Cyclooxygenase-2 Expression in Acute Respiratory Distress Syndrome", The Journal of Immunology, 2017, vol. 199, Iss. 6, pp. 2043-2054.

Holland et al., "An official European Respiratory Society/American Thoracic Society technical standard: field walking tests in chronic respiratory disease", European Respiratory Journal, 2014, vol. 44, Iss. 6, pp. 1428-1446.

Shimazaki et al., "Diketopiperazine Derivatives, a New Series of Platelet-Activating Factor Inhibitors," Chem. Pharm. Bull., 1987, vol. 35(8), pp. 3527-3530.

Shimazaki et al., "Diketopiperazines as a New Class of Platelet-Activating Factor Inhibitors," J. Med. Chem., 1987, vol. 30, pp. 1706-1709.

Shimazaki et al., "PAF Inhibitory Activity of Diketopiperazines: Structure-Activity Relationships," Lipids, 1991, vol. 26(12), pp. 1175-1178.

Smith et al., "Solid-phase synthesis of a library of piperazinediones and diazepinediones via Kaiser oxime resin." Bioorg. Med. Chem., 1998, vol. 8, pp. 2369-2374.

World Health Organization, "WHO R&D Blueprint: novel Coronavirus: COVID-19 Therapeutic Trial Synopsis", 2020, 12 pages.

Yoshida et al., "PAF Inhibitors of Microbial Origin," Prog. Biochem. Pharmacol., 1988, vol. 22, pp. 68-80.

Wikipedia, "COVID-19", Mar. 17, 2020 (retrieved May 7, 2021). Retrieved from: en.wikipedia.org/w/index.php?title=COVID-19&oldid=946010373.

International Search Report and Written Opinion for International (PCT) Patent Application No. PCT/US21/23960 dated Jun. 4, 2021, 9 pages.

\* cited by examiner

METHODS FOR TREATING DISEASES ASSOCIATED WITH RESPIRATORY VIRUSES

CROSS REFERENCE TO RELATED APPLICATIONS

This application claims the benefit of U.S. Provisional Patent Application No. 62/994,171, filed Mar. 24, 2020, the disclosure of which is incorporated herein by reference in its entirety.

FIELD

The present disclosure relates to a method of treating diseases associated with respiratory viruses, also referred to herein as viral respiratory diseases. The method comprises administering an effective amount of a pharmaceutical composition prepared by removing albumin from a solution of a human serum albumin composition and/or comprising a diketopiperazine with amino acid side chains of aspartic acid and alanine (DA-DKP). The present disclosure also provides a pharmaceutical product comprising DA-DKP, in some embodiments in a nebulized form.

BACKGROUND

Common viral respiratory diseases are illnesses caused by a variety of viruses that have similar traits and affect the upper respiratory tract. The viruses involved may be the coronaviruses, influenza viruses, respiratory syncytial virus (RSV), parainfluenza viruses, or respiratory adenoviruses. Coronaviruses are a group of related viruses that cause diseases in mammals and birds. In humans, coronaviruses cause respiratory tract infections that can be mild, such as some cases of the common cold (among other possible causes, predominantly rhinoviruses), and others that can be lethal, such as SARS, MERS, and COVID-19. Symptoms in other species vary: in chickens, they cause an upper respiratory tract disease, while in cows and pigs they cause diarrhea.

Diketopiperazines have been reported to exhibit a variety of biological activities. See, e.g., U.S. Pat. No. 4,289,759 (immunoregulatory agents), U.S. Pat. No. 4,331,595 (immunoregulatory agents), U.S. Pat. No. 4,940,709 (PAF antagonists), U.S. Pat. No. 5,700,804 (inhibitors of plasminogen activator inhibitor), U.S. Pat. No. 5,750,530 (inhibitors of plasminogen activator inhibitor) and U.S. Pat. No. 5,990,112 (inhibitors of metalloproteases); PCT publication nos. WO 97/36888 (inhibitors of farnesyl-protein transferase) and WO 99/40931 (treatment of central nervous system injury); EP Patent No. 0043219 (immunoregulatory agents); Japanese patent application nos. 63 290868 (PAF antagonists) and 31 76478 (immunosuppressive agents); and Shimazaki et al., Chem. Pharm. Bull., 35(8), 3527-3530 (1987) (PAF antagonists), Shimazaki et al., J. Med. Chem., 30, 1709-1711 (1987) (PAF antagonists), Shimazaki et al., Lipids, 26(12), 1175-1178 (1991) (PAF antagonists), Yoshida et al., Prog. Biochem. Pharmacol., 22, 68-80 (1988) (PAF antagonists), Alvarez et al., J. Antibiotics, 47(11), 1195-1201 (1994) (inhibitors of calpain).

SUMMARY

In a first aspect, the present disclosure provides a method of treating or preventing one or more symptoms of a viral respiratory disease in a patient, comprising administering to the patient a pharmaceutical composition prepared by removing albumin from a solution of a human serum albumin composition.

In a second aspect, the present disclosure provides a method of treating or preventing a viral respiratory disease in a patient, comprising administering to the patient a pharmaceutical composition comprising DA-DKP.

In a third aspect, the present disclosure provides a method of treating or preventing inflammation associated with a viral respiratory disease in a patient, comprising administering to the patient a pharmaceutical composition prepared by removing albumin from a solution of a human serum albumin composition.

In a fourth aspect, the present disclosure provides a method of treating or preventing inflammation associated with a viral respiratory disease in a patient, comprising administering to the patient a pharmaceutical composition comprising DA-DKP.

In some embodiments the viral respiratory disease is selected from the group consisting of Severe Acute Respiratory Distress Syndrome (SARS), Middle East Respiratory Syndrome (MERS), COVID-19, and a viral infection associated with asthma, pneumonia, bronchitis and/or tuberculosis. In some embodiments, the viral respiratory disease is COVID-19.

In some embodiments the viral respiratory disease is caused by a virus selected from group consisting of a coronavirus, an influenza virus, respiratory syncytial virus (RSV), a parainfluenza virus, and a respiratory adenovirus. The virus is, in some embodiments, selected from the group consisting of SARS-Coronavirus-2 (SARS-CoV-2), SARS-associated coronavirus (SARS-CoV), and Middle East Respiratory Syndrome Coronavirus (MERS-CoV). In some aspects the method of claim 8, wherein the virus is SARS-Coronavirus-2 (SARS-CoV-2).

In some embodiments the patient has or is at risk of developing inflammation of a tissue selected from the group consisting of lung, brain, heart, kidney, blood vessel, skin, and nerve. In some embodiments, the tissue is lung.

In some embodiments the patient has or is at risk of developing a symptom selected from the group consisting of acute respiratory distress syndrome (ARDS), acute lung injury (ALI), interstitial lung disease, pulmonary fibrosis, pneumonia, and reactive airway disease syndrome.

In some embodiments the patient has or is at risk of developing a symptom selected from the group consisting of fatigue, shortness of breath or difficulty breathing, low exercise tolerance, low blood oxygen saturation, cough, sore throat, stuffy or runny nose, joint pain, chest pain, tightness or discomfort, muscle pain, muscle weakness, fever, heart palpitations, difficulty thinking and/or concentrating, and depression.

In some embodiments the patient has experienced the symptom at least four weeks, at least one month, at least two months, or at least three months.

In some embodiments the administering results in an outcome selected from the group consisting of reduced ventilator time, reduced mortality, improvement in oxygenation parameters, reduced time to resolution of one or more respiratory symptoms, improved pulmonary function, and combinations thereof.

In certain embodiments, after the administration, the patient achieves improvement on the World Health Organization COVID-19 ordinal scale of at least 4, at least 3, at least 2, or at least 1 (World Health Organization. (2020).

WHO R&D Blueprint: novel Coronavirus: COVID-19 Therapeutic Trial Synopsis, Feb. 18, 2020, Geneva, Switzerland).

In some embodiments the patient has respiratory distress, and in certain embodiments the patient requires supplemental oxygen.

In some embodiments the pharmaceutical composition reduces vascular permeability in the patient, increases the production of lung prostaglandins in the patient, and/or decreases the amount or activity of one or more lung inflammatory signaling proteins in the patient. In certain aspects the one or more lung inflammatory signaling proteins is/are selected from the group consisting of TNF-alpha, IL6 and CXCL10.

In some embodiments the composition is administered in a form suitable for administration to the lung. In some embodiments composition is administered in a nebulized form.

In some embodiments the composition is administered at a dose of 8 milliliters, and in some embodiments the composition is administered quater in die. In some embodiments the composition is administered at a dose of 8 milliliters quater in die. In some embodiments the composition is administered for five days.

In some embodiments the composition is administered in an aerosolized form.

In some embodiments the composition is administered intravenously. In some embodiments the composition is administered at a dose of 250 cubic centimeters, and in some embodiments the composition is administered bis in die. In certain embodiments the composition is administered at a dose of 250 cubic centimeters bis in die. In some embodiments the composition is administered for five days.

In some embodiments the composition comprises DA-DKP, and in some embodiments the composition further comprises N-acetyl-tryptophan (NAT), caprylic acid, caprylate or combinations thereof. In some embodiments the DA-DKP is in a composition prepared by removing albumin from a solution of a human serum albumin composition. In some embodiments removing the albumin comprises treating the human serum albumin composition by a separation method selected from the group consisting of ultrafiltration, sucrose gradient centrifugation, chromatography, salt precipitation, and sonication. In some embodiments the removing comprises passing the human serum albumin composition over an ultrafiltration membrane with a molecular weight cut off that retains the albumin, and wherein the resulting filtrate comprises DA-DKP. In certain aspects the ultrafiltration membrane has a molecular weight cutoff of less than 50 kDa, less than 40 kDa, less than 30 kDa, less than 20 kDa, less than 10 kDa, less than 5 kDa or less than 3 kDa.

In a fifth aspect, the present disclosure provides a pharmaceutical product comprising a DA-DKP-containing composition, formulated for administration in some embodiments by nebulization or aerosolization, and in some embodiments formulated for intravenous administration. In some embodiments the DA-DKP is prepared by removing albumin from a solution of a human serum albumin composition. In certain embodiments removing the albumin comprises treating the human serum albumin composition by a separation method selected from the group consisting of ultrafiltration, sucrose gradient centrifugation, chromatography, salt precipitation, and sonication. In some embodiments the removing comprises passing the human serum albumin composition over an ultrafiltration membrane with a molecular weight cut off that retains the albumin, and wherein the resulting filtrate comprises DA-DKP. In some embodiments the ultrafiltration membrane has a molecular weight cutoff of less than 50 kDa, less than 40 kDa, less than 30 kDa, less than 20 kDa, less than 10 kDa, less than 5 kDa or less than 3 kDa. In certain aspects the DA-DKP-containing composition further comprises NAT, caprylic acid, caprylate and combinations thereof.

Some embodiments include of the pharmaceutical composition include a pharmaceutically-acceptable carrier.

In a sixth aspect, the present disclosure provides a kit comprising a pharmaceutical product comprising a DA-DKP-containing composition formulated for administration by nebulization or aerosolization. In some embodiments the kit comprising a pharmaceutical product comprising a DA-DKP-containing composition formulated for intravenous administration. In certain embodiments the DA-DKP is prepared by removing albumin from a solution of a human serum albumin composition.

DETAILED DESCRIPTION

The present disclosure generally relates to a method of treating a viral respiratory disease. The treatment comprises administering an effective amount of a pharmaceutical composition prepared by removing albumin from a solution of a human serum albumin composition and/or comprising aspartyl-alanyl diketopiperazine (DA-DKP) to an animal having a need thereof.

The present disclosure also relates to a method of reducing lung inflammation associated with a viral infection in an animal in need thereof. The method comprises administering an effective amount of a pharmaceutical composition comprising DA-DKP to an animal having a need thereof.

The present disclosure further relates to a method of reducing vascular permeability in lungs of an animal in need thereof. The method comprises administering an effective amount of a pharmaceutical composition comprising DA-DKP to an animal having a need thereof.

The present disclosure also relates to a method to up regulate the production of lung prostaglandins in an animal in need thereof. The method comprises administering an effective amount of a pharmaceutical composition comprising DA-DKP to an animal having a need thereof.

The present disclosure further relates to a method to down regulate one or more lung inflammatory signaling proteins in a subject in need thereof. The method comprises administering an effective amount of a pharmaceutical composition comprising DA-DKP to an animal having a need thereof. In one aspect, the lung inflammatory signaling protein is TNF-alpha, interleukin-6 (IL6) and C-X-C motif chemokine ligand 10 (CXCL10).

The present disclosure also provides for a pharmaceutical product comprising a DA-DKP composition formulated for administration to the lungs, including a nebulized form or aerosolized form. The DA-DKP of the product may be prepared by removing albumin from a solution of human serum albumin.

The present disclosure also provides for kit comprising a DA-DKP composition formulated for administration to the lungs, including a nebulized form or aerosolized form.

DA-DKP has multiple anti-inflammatory and immune modulating effects including inhibition of multiple pro-inflammatory cytokines, chemokines and signaling molecules at the transcription level, inhibition of the migration and adhesion of T-cells and monocytes, activity at the G-coupled protein receptor level, activity on actin-dependent cytoskeletal events, and reduction in vascular permeability and inhibition of inflammation induced by platelet activating factor, among other effects. Because inflammation is exacerbated by, or involves, activated T-cells, the composition of the present disclosure comprising DA-DKP can be used to treat lung inflammatory diseases and/or inflammation related to viral respiratory diseases and/or to prevent lung inflammation and lung inflammatory diseases related to viral respiratory diseases. Thus, one embodiment of the present disclosure is a method of reducing inflammation caused by a viral respiratory disease in an individual.

The pharmaceutical composition comprising DA-DKP can be prepared by removing albumin from a solution of human serum albumin as disclosed herein.

A viral respiratory disease is an illness caused by a virus and affects the respiratory tract. Such viral respiratory diseases can include Severe Acute Respiratory Distress Syndrome (SARS), Middle East Respiratory Syndrome (MERS), COVID-19, and viral infection associated with asthma, pneumonia, bronchitis and/or tuberculosis. Viruses that can cause one or more viral respiratory diseases include coronaviruses, influenza viruses, respiratory syncytial virus (RSV), parainfluenza viruses, and respiratory adenoviruses. Coronaviruses include SARS-Coronavirus-2 (SARS-CoV-2), SARS-associated coronavirus (SARS-CoV), and Middle East Respiratory Syndrome Coronavirus (MERS-CoV). Coronavirus infections and other viral infections can cause acute respiratory distress syndrome (ARDS), acute lung injury (ALI), interstitial lung disease, pulmonary fibrosis, pneumonia, and reactive airway disease syndrome. Coronavirus infections and other viral infections can cause inflammation in tissues such as lung, brain, heart, kidney, blood vessel, skin, and nerve. Coronavirus infections and other viral infections can cause symptoms such as fatigue, shortness of breath or difficulty breathing, low exercise tolerance, low blood oxygen saturation, cough, sore throat, stuffy or runny nose, joint pain, chest pain, tightness, or discomfort, muscle pain, muscle weakness, fever, heart palpitations, difficulty thinking and/or concentrating, and depression.

COVID-19 infection is a respiratory illness caused by the novel coronavirus SARS-COV-2 and has been classified as a pandemic with no known cure to date. COVID-19 is detected and diagnosed with a laboratory test. The primary symptoms of COVID-19 infection include mild symptoms such as fever, cough, chills, muscle pain, headache, gastrointestinal symptoms, and the loss of taste or smell. Once infected, the virus moves down a patient's respiratory tract, where the lungs may become inflamed, making breathing difficult and sometimes requiring supplemental oxygen in the more severe cases of the disease.

Respiratory symptoms after a COVID-19 infection include shortness of breath, cough, chest discomfort, low exercise tolerance and low oxygen saturation, all of which point to potential inflammation related complication sequalae. Infiltrating or resident cells in the immune system (e.g., macrophages, peripheral blood mononuclear cells, etc.) may be responsible for the development of these respiratory long-term consequences. Chronic or prolonged inflammation of the lungs maybe responsible for a myriad of respiratory signs and symptoms experienced by patients after a COVID-19 infection. Chest x-rays and CT scans reveal disturbing patterns of perhaps extensive fibrosis and potential loss of elasticity and oxygen diffusion capacity.

The SARS-Cov-2 virus transmits through the respiratory system and can cause a severe dysregulation of the immune response and damage in the lungs. Chronic, prolonged inflammation of the lungs may be responsible for a myriad of continuing respiratory signs and symptoms post-infection, including cough, shortness of breath, chest discomfort, low exercise tolerance and low blood oxygen saturation. The continued hyperinflammatory state is thought to lead to prolonged clinical complications, and treatment with immunomodulators at this later point in the disease is more effective than anti-viral treatment.

Inflammation associated with COVID-19 may trigger even more severe complications including pneumonia, acute lung injury (ALI) and/or acute respiratory distress syndrome (ARDS), which is a leading cause of mortality in COVID-19. ARDS is associated with widespread inflammation in the lungs. The underlying mechanism of ARDS involves diffuse injury to cells which form the barrier of the microscopic air sacs (alveoli) of the lung, surfactant dysfunction, and activation of the immune system. The fluid accumulation in the lungs associated with ARDS is partially explained by vascular leakage due to inflammation.

As disclosed herein, the composition of the present disclosure, in an aqueous solution that can be delivered through nebulization, can be used for suppressing inflammation in the lungs, thus making it a therapy for ARDS. An important aspect of ARDS, triggered by COVID-19, is an initial release of chemical signals and other inflammatory mediators secreted by lung epithelial and endothelial cells. Neutrophils and some T-lymphocytes migrate into the inflamed lung tissue and contribute to the amplification/deterioration of ARDS. A decrease in the production of lipid mediators of inflammation (prostaglandins) may impair the resolution of inflammation associated with ARDS (Fukunaga, et. al., *Cyclooxygenase 2 Plays a Pivotal Role in the Resolution of Acute Lung Injury*. Journal of Immunology 2005; 174:5033-5039.; Gao et al J Immunol 2017; 199:2043-2054).

The World Health Organization (WHO)'s Clinical Care for Severe Acute Respiratory Infection: COVID-19 Adaptation recommends early intervention with supplemental oxygen for COVID-19 patients with low blood oxygen saturation ($SpO_2$) beginning with the least invasive modality possible (e.g. hand-held oxygen source) and moving to more invasive modalities (e.g. bilevel positive airway pressure [BiPAP] and/or non-invasive ventilation (NIV)) as severity increases. Treatment during early intervention for COVID-19 patients with respiratory distress requires monitoring of respiratory function with treatment responsive to disease progression. The CDC recommends following the guidelines for treatment of COVID-19 patients with hypoxia in Surviving Sepsis Campaign: Guidelines on the Management of Critically Ill Adults with Coronavirus Disease 2019 (COVID-19).

Patients who fail to respond to less-invasive treatment are at a high risk of developing ARDS, a rapidly progressive disease characterized by widespread inflammation in the lungs that results in flooding of the lungs' microscopic air sacs, which are responsible for the exchange of gases such as oxygen and carbon dioxide with capillaries in the lungs. Additional common findings in ARDS include partial collapse of the lungs (atelectasis) and low levels of oxygen in the blood (hypoxemia). The clinical syndrome is associated with pathological findings including pneumonia and diffuse alveolar damage, the latter of which is characterized by diffuse inflammation of lung tissue. The triggering insult to the tissue usually results in an initial release of chemical signals and other inflammatory mediators secreted by local epithelial and endothelial cells.

ARDS impairs the lungs' ability to exchange oxygen and carbon dioxide. The underlying mechanism of ARDS involves diffuse injury to cells that form the barrier of the microscopic air sacs of the lungs, surfactant dysfunction, activation of the immune system, and dysfunction of the body's regulation of blood clotting.

Diagnosis of ARDS is based on the 2012 Berlin definition:
- lung injury of acute onset, within 1 week of an apparent clinical insult and with progression of respiratory symptoms
- bilateral opacities on chest imaging (chest radiograph or CT) not explained by other lung pathology (e.g. effusion, lobar/lung collapse, or nodules)
- respiratory failure not explained by heart failure or volume overload
- decreased ratio of partial pressure arterial oxygen ($PaO_2$) to fraction of inspired oxygen ($FiO_2$) of less than or equal to 300 mm Hg despite a positive end-expiratory pressure (PEEP) of more than 5 cm $H_2O$.

The severity of ARDS is defined by the Berlin definition as:
- mild ARDS: 201-300 mmHg (≤39.9 kPa)
- moderate ARDS: 101-200 mmHg (≤26.6 kPa)
- severe ARDS: ≤100 mmHg (≤13.3 kPa)

There are no approved treatments for ARDS, and standard of care (SOC) is supportive management.

Furthermore, COVID-19 can cause prolonged symptoms even after the viral infection has seemingly been cleared. These prolonged effects are referred to a post-COVID, post-acute COVID, post-acute sequelae of SARS-CoV-2 infection (PASC), chronic COVID syndrome (CCS), and long-haul COVID. The many symptoms can include fatigue, shortness of breath or difficulty breathing, low exercise tolerance, low blood oxygen saturation, cough, sore throat, stuffy or runny nose, joint pain, chest pain, tightness or discomfort, muscle pain, muscle weakness, fever, heart palpitations, difficulty thinking and/or concentrating, and depression. Symptoms can also include breathlessness, myalgia, anxiety, extreme fatigue, low mood, sleep disturbances or difficulty sleeping, and memory impairment. Other neurologic symptoms include brain fog (non-specific cognitive problems), headache, numbness or tingling, dysgeusia, dizziness, pain, blurred vision, tinnitus, and loss of taste (ageusia) or smell (anosmia). Symptoms can last for a month or more, including at least 1, at least 2, at least 3, at least 4, at least 5, at least 6, at least 7, at least 8, at least 9, at least 10, at least 11, at least 12 months, or longer. The continued hyperinflammatory state is thought to lead to prolonged clinical complications, and treatment with immunomodulators at this later point in the disease is more effective than anti-viral treatment.

In addition to lung symptoms and long COVID, SARS-CoV-2 infection can lead to damage to other organs, including the heart and kidneys. SARS-CoV-2 infects endothelial cells and also leads to systemic inflammation, causing vasculopathy that affects widespread parts of the body. The vasculopathy or other phenomena can cause damage to the heart (myocarditis or arrhythmia), kidneys (acute kidney injury, chronic kidney disease, or renal failure), liver (liver dysfunction), blood vessels (bleeding and blood clots), skin (Kawasaki-like syndrome, rash, hair loss, and urticarial, vesicular, purpuric, and papulosquamous lesions), digestive system (anorexia, nausea, vomiting, diarrhea, and abdominal pain), brain (described above), and nerves (symptoms described above and cerebrovascular disease, ataxia, seizure, vision impairment, and nerve pain). Other symptoms include lymphopenia, hypoxia, blood hypercoagulability, multi-organ failure, sepsis, and septic shock.

Conventional pharmaceutical therapies for viral respiratory disease include anti-viral compositions such as amantadine and ribavin.

In any of the methods and compositions disclosed herein, forms for administration of the composition of the present disclosure include nebulized form, aerosolized form, sprays, drops, and powders. The active ingredient may be mixed under sterile conditions with a pharmaceutically-acceptable carrier, and with any buffers, or propellants which may be required. In some embodiments, the form for administration is a sterile liquid that is administered as a nebulized liquid form or intravenously.

Aerosol (inhalation) delivery can be performed using methods standard in the art. Carriers suitable for aerosol delivery are described herein. Devices for delivery of aerosolized formulations include, but are not limited to, pressurized metered dose inhalers (MDI), dry powder inhalers (DPI), and metered solution devices (MSI), and include devices that are nebulizers and inhalers.

The composition of the present disclosure comprising DA-DKP can be administered to an animal by any suitable route of administration to the lungs, including nasal, intratracheal, bronchial, direct instillation into the lung, inhaled and oral.

"Treat" is used herein to mean to reduce (wholly or partially) the symptoms, duration or severity of a disease. In accordance with the present state of the art, treat typically does not mean to cure. As provided for herein, in any of the methods disclosed herein treating includes that the animal experiences an outcome including, but not limited to, reduced ventilator time, reduced mortality, improvement in oxygenation parameters and combinations thereof.

The pharmaceutical composition comprising DA-DKP of the present disclosure is administered to an animal in need of treatment. In some embodiments, the animal is a mammal, such as a rabbit, goat, dog, cat, horse or human. In some embodiments, the animal in need of treatment is a human. Effective dosage amounts may vary with the severity of the disease or condition, the route(s) of administration, the duration of the treatment, the identity of any other drugs being administered to the animal, the age, size and species of the animal, the discretion of the prescribing health care provider, and like factors known in the medical and veterinary arts.

The composition of the present disclosure may be a pharmaceutical solution having a DA-DKP concentration range with a lower endpoint of about 10 μM, about 20 μM, about 30 μM, about 40 μM, about 50 μM, about 60 μM, about 70 μM, about 80 μM, about 90 μM, about 100 μM, about 110 μM, about 120 μM, about 130 μM, about 140 μM, about 150 μM, about 160 μM, about 170 μM, about 180 μM, about 190 μM, about 200 μM, about 210 μM, about 220 μM, about 230 μM, about 240 μM, about 240, about 250 μM, about 260 μM, about 270 μM, about 280 μM, about 290 μM, about 300 μM, about 310, about 320 μM, about 330 μM, about 340 μM, about 350 μM, about 360 μM, about 370 μM, about 380 μM, about 390 μM, or about 400 μM. The composition of the present disclosure may be a pharmaceutical solution having a DA-DKP concentration range with an upper endpoint of about 600 μM, about 580 μM, about 570 μM, about 560 μM, about 550 μM, about 540 μM, about 530 μM, about 520 μM, about 510 μM, about 500 μM, about 490 μM, about 480 μM, about 470 μM, about 460 μM, about 450 μM, about 440 μM, about 430 μM, about 420 μM, about 410 μM, about 400 μM, about 390 μM, about 380 μM, about 370 μM, about 360 μM, about 350, about 340 μM, about 330 μM, about 320 μM, about 310 μM, about 300 μM, about 290 μM, about 280, about 270 µM, about 260 µM, about 250 µM, about 240 µM, about 230 µM, about 220 µM, about 210 µM, or about 200 µM.

An effective amount of DA-DKP in the composition of the present disclosure for treating a viral respiratory disease or condition can be a range with a lower endpoint of about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, about 260 µg, about 270 µg, about 280 µg, about 290 µg, about 300 µg, about 310 µg, about 320 µg, about 330 µg, about 340 µg, about 350 µg, about 360 µg, about 370 µg, about 380 µg, about 390 µg, about 400 µg, about 425 µg, about 450 µg, about 475 µg or about 500 µg. In addition, an effective amount of DA-DKP in the composition of the present disclosure for treating a viral respiratory disease or condition can be a range with upper endpoint of about 500 µg, about 490 µg, about 480 µg, about 470 µg, about 460 µg, about 450 µg, about 440 µg, about 430 µg, about 420 µg, about 410 µg, about 400 µg, about 390 µg, about 380 µg, about 370 µg, about 360 µg, about 350 µg, about 340 µg, about 330 µg, about 320 µg, about 310 µg, about 300 µg, about 290 µg, about 280 µg, about 270 µg, about 260 µg, about 250 µg, about 240 µg, about 230 µg, about 220 µg, about 210 µg, about 200 µg, about 190 µg, about 180 µg, about 170 µg, about 160 µg, about 150 µg, about 140 µg, about 130 µg, about 120 µg, about 110 µg, about 100 µg, about 90 µg, about 80 µg, about 70 µg, about 60 µg, about 50 µg, about 40 µg, about 30 µg, or about 20 µg.

Different doses of the disclosed compositions can be used with different routes of administration. Administration to the lung, for example by nebulizer, can involve doses of about 1, about 2, about 3, about 4, about 5, about 6, about 7, about 8, about 9, about 10, about 11, about 12, about 13, about 14, about 15, about 16, about 17, about 18, about 19, or about 20 milliliters. Intravenous administration can involve doses of about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 260, about 270, about 275, about 280, about 290, about 300, about 310, about 320, about 330, about 340, about 350, about 360, about 370, about 375, about 380, about 390, about 400, about 425, about 450, about 475, about 500, about 525, about 550, about 575, about 600, about 650, about 700, about 750, about 800, about 850, about 900, about 950, about 1000, about 1100, about 1200, about 1300, about 1400, or about 1500 milliliters (or cubic centimeters). The disclosed compositions can be administered 1, 2, 3, 4, 5, 6, 7, 8, or more times per day for 1, 2, 3, 4, 5, 6, 7, 8, 9, 10, 11, 12, 13, or 14 days. Disclosed compositions can also be administered for 3, 4, 5, 6, 7, 8, 9, 10, 11, or 12 weeks, and/or for 4, 5, 6, 7, 8, 9, 10, 11, or 12 months or more.

While it is possible for a compound of the present disclosure, such as DA-DKP, to be administered alone, in many embodiments the compound is administered as a pharmaceutical formulation (composition). The pharmaceutical compositions of the present disclosure comprise a compound or compounds of the present disclosure as an active ingredient in admixture with one or more pharmaceutically-acceptable carriers and, optionally, with one or more other compounds, drugs or other materials. In some embodiments, the compound is DA-DKP. Each carrier is advantageously "acceptable" in the sense of being compatible with the other ingredients of the formulation and not injurious to the animal. Pharmaceutically-acceptable carriers are well known in the art. Regardless of the route of administration selected, the compounds of the present disclosure are formulated into pharmaceutically-acceptable dosage forms by conventional methods known to those of skill in the art. See, e.g., Remington's Pharmaceutical Sciences (Easton, Pa.: Mack Pub. Co, 1965. Print; $23^{rd}$ Ed. (2020) ISBN: 9780128200070).

Examples of suitable aqueous and nonaqueous carriers which may be employed in the pharmaceutical compositions of the present disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

The formulations may be presented in unit-dose or multi-dose sealed containers, for example, ampoules and vials, and may be stored in a lyophilized condition requiring only the addition of the sterile liquid carrier, for example water for nebulization, immediately prior to use.

Kits comprising the pharmaceutical products of the present disclosure are also provided. The kits can comprise a DA-DKP composition formulated for administration to the lung including a nebulized form and/or an aerosolized form. The DA-DKP can be prepared as described herein, such as by removing albumin from a solution of a human albumin composition. The kits may contain unit-dose or multi-dose sealed containers, for example, ampoules and vials, and may be stored in a lyophilized condition requiring only the addition of the sterile liquid carrier, for example water, immediately prior to use. The kits may also be stored in a condition, wherein the contents are ready for direct use or injection.

The composition of the present disclosure may further comprise N-acetyl-tryptophan (NAT), caprylic acid, caprylate or combinations thereof. In some embodiments, the composition comprises NAT. Compositions of the present disclosure having NAT, caprylic acid, caprylate or combinations thereof have a concentration range with a lower endpoint of about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, or about 20 mM. In addition, compositions of the present disclosure having NAT, caprylic acid, caprylate or combinations thereof have a concentration range with an upper endpoint of about 40 mM, about 39 mM, about 38 mM, about 37 mM, about 36 mM, about 35 mM, about 34 mM, about 33 mM, about 32 mM, about 31 mM, about 30 mM, about 29 mM, about 28 mM, about 27 mM, about 26 mM, about 25 mM, about 24 mM, about 23 mM, about 22, or about 21 mM. In some embodiments, the concentration range is about 4 mM to about 20 mM.

In addition, the composition of the present disclosure can also comprise a second drug such as an anti-viral, an antibiotic, chloroquine, hydroxychloroquine, known drugs for treating pneumonia, an analgesic (such as lidocaine or paracetamol), an anti-inflammatory (such as corticosteroids, such as dexamethasone and betamethasone, non-steroid anti-inflammatory drugs (NSAIDs), ibuprofen, naproxen), and/or other suitable drugs.

Methods of making diketopiperazines, such as DA-DKP, are well known in the art, and these methods may be employed to synthesize the diketopiperazines of the present disclosure. See, e.g., U.S. Pat. Nos. 4,694,081, 5,817,751, 5,990,112, 5,932,579 and 6,555,543, US Patent Application Publication Number 2004/0024180, PCT applications WO 96/00391 and WO 97/48685, and Smith et al., Bioorg. Med. Chem. Letters, 8, 2369-2374 (1998).

For instance, diketopiperazines, such as DA-DKP, can be prepared by first synthesizing dipeptides. The dipeptides can be synthesized by methods well known in the art using L-amino acids, D-amino acids or a combination of D- and L-amino acids. In some embodiments solid-phase peptide synthetic methods are employed. Of course, dipeptides are also available commercially from numerous sources, including DMI Synthesis Ltd., Cardiff, UK (custom synthesis), Sigma-Aldrich, St. Louis, Mo. (primarily custom synthesis), Phoenix Pharmaceuticals, Inc., Belmont, Calif. (custom synthesis), Fisher Scientific (custom synthesis) and Advanced ChemTech, Louisville, Ky.

Once the dipeptide is synthesized or purchased, it is cyclized to form a diketopiperazine. This can be accomplished by a variety of techniques. For example, U.S. Patent Application Publication Number 2004/0024180 describes a method of cyclizing dipeptides. Briefly, the dipeptide is heated in an organic solvent while removing water by distillation. In some embodiments, the organic solvent is a low-boiling azeotrope with water, such as acetonitrile, allyl alcohol, benzene, benzyl alcohol, n-butanol, 2-butanol, t-butanol, acetic acid butylester, carbon tetrachloride, chlorobenzene chloroform, cyclohexane, 1,2-dichlorethane, diethylacetal, dimethylacetal, acetic acid ethylester, heptane, methylisobutylketone, 3-pentanol, toluene and xylene. The temperature depends on the reaction speed at which the cyclization takes place and on the type of azeotroping agent used. In some embodiments, the reaction is carried out at 50-200° C., in some embodiments at 80-150° C. The pH range in which cyclization takes place can be easily determine by the person skilled in the art. In some embodiments the pH range will advantageously be 2-9, in some embodiments 3-7.

When one or both of the amino acids of the dipeptide has, or is derivatized to have, a carboxyl group on its side chain (e.g., aspartic acid or glutamic acid), the dipeptide is cyclized as described in U.S. Pat. No. 6,555,543. Briefly, the dipeptide, with the side-chain carboxyl still protected, is heated under neutral conditions. Typically, the dipeptide will be heated at from about 80° C. to about 180° C., in some embodiments at about 120° C. The solvent will be a neutral solvent. For instance, the solvent may comprise an alcohol (such as butanol, methanol, ethanol, and higher alcohols, but not phenol) and an azeotropic co-solvent (such as toluene, benzene, or xylene). In some embodiments, the alcohol is butan-2-ol, and the azeotropic co-solvent is toluene. The heating is continued until the reaction is complete, and such times can be determined empirically. Typically, the dipeptide will be cyclized by refluxing it for about 8-24 hours, in some embodiments about 18 hours. Finally, the protecting group is removed from the diketopiperazine. In doing so, the use of strong acids (mineral acids, such as sulfuric or hydrochloric acids), strong bases (alkaline bases, such as potassium hydroxide or sodium hydroxide), and strong reducing agents (e.g., lithium aluminum hydride) should be avoided, in order to maintain the chirality of the final compound.

Dipeptides made on solid phase resins can be cyclized and released from the resin in one step. See, e.g., U.S. Pat. No. 5,817,751. For instance, the resin having an N-alkylated dipeptide attached is suspended in toluene or toluene/ethanol in the presence of acetic acid (e.g., 1%) or triethylamine (e.g., 4%). Typically, basic cyclization conditions are utilized for their faster cyclization times.

Other methods of cyclizing dipeptides and of making diketopiperazines are known in the art and can be used in the preparation of diketopiperazines useful in the practice of the present disclosure. See, e.g., those references listed above. In addition, many diketopiperazines suitable for use in the present disclosure can be made as described below from proteins and peptides. Further, diketopiperazines for use in the practice of the present disclosure can be obtained commercially from, e.g., DMI Synthesis Ltd., Cardiff, UK (custom synthesis).

The DA-DKP composition and/or products of the present disclosure can be prepared from solutions containing DA-DKP, including from the commercially-available pharmaceutical compositions comprising albumin, such as human serum albumin, by well known methods, such as ultrafiltration, chromatography, size-exclusion chromatography (e.g., Centricon filtration), affinity chromatography (e.g., using a column of beads having attached thereto an antibody or antibodies directed to the desired diketopiperazine(s) or an antibody or antibodies directed to the truncated protein or peptide), anion exchange or cation exchange, sucrose gradient centrifugation, salt precipitation, or sonication, that will remove some or all of the albumin in the solution. The resultant DA-DKP-containing composition and/or product can be used and incorporated into pharmaceutical compositions as described above.

Using an ultrafiltration separation method, a human serum albumin composition can be passed over an ultrafiltration membrane having a molecular weight cut-off that retains the albumin while the DA-DKP passes into the resulting filtrate or fraction. This filtrate may comprise components having molecular weights less than about 50 kDa, less than about 40 kDa, less than 30 kDa, less than about 20 kDa, less than about 10 kDa, less than about 5 kDa, less than about 3 kDa. In some embodiments, the filtrate comprises components having molecular weights less than about 5 kDa (also referred to as "<5000 MW" and/or low molecular weight fraction "LMWF"). This <5000MW fraction or filtrate contains DA-DKP which is formed after the dipeptide aspartate-alanine is cleaved from albumin and subsequently cyclized into the diketopiperazine.

The term "LMWF" refers to a low molecular weight fraction of HSA that is a composition prepared by separation of high molecular weight components from human serum albumin (HSA). For example, LMWF can be prepared by filtration of a commercially available HSA solution wherein molecular weight components of more than 3 kilo daltons (kDa), 5 kDa, 10 kDa, 20 kDa, 30 kDa, 40 kDa, 50 kDa, are separated from the HSA solution. Alternatively, the term LMWF can refer to a composition prepared by separation of the high molecular weight components by other techniques, including but not limited to ultrafiltration, column chromatography including size exclusion chromatography, affinity chromatography, anion exchange, cation exchange, sucrose gradient centrifugation, salt precipitation, or sonication. LMWF also refers to a composition that includes components of HSA having a molecular weight less than 50,000 daltons (Da) (or 50 kDa), 40 kDa, 30 kDa, 20 kDa, 10 kDa, 5000 Da, 4000 Da, or 3000 Da (corresponding to 50,000 g/mol, 40,000 g/ml, 30,000 g/mol, 20.00 g/mol, 10,000 g/mol, 5,000 g/mol, 4,000 g/mol or 3,000 g/mol respectively). AMPION® (Ampio Pharmaceuticals, Inc., Englewood, Colo. USA) is a <5 kDa fraction of human serum albumin (HSA). AMPION® can be produced, for example, by filtering commercially available HSA as described herein. Commercially available HSA is produced by fractionation of blood, for example by the Cohn process or its variations. AMPION® can be produced by filtering such commercially available HSA, for example a 5% HSA solution, to remove components above 5 kDA.

AMPION® is currently approved for clinical use by the United States Food and Drug Administration, as an anti-inflammatory, immunomodulating drug. The novel mode of action of AMPION® involves multiple biochemical pathways associated with resolving inflammation. AMPION® is a suitable drug for the treatment of viral diseases for several reasons, including but not limited to those below.

First, an important aspect of ARDS, triggered by COVID-19, is an initial release of chemical signals and other inflammatory mediators secreted by lung epithelial and endothelial cells. Neutrophils and some T-lymphocytes migrate into the inflamed lung tissue and contribute to the amplification/deterioration of ARDS. A decrease in the production of lipid mediators of inflammation (prostaglandins) may impair the resolution of inflammation associated with ARDS.

Second, AMPION® was reported to up regulate the production of these healing lipid mediators' prostaglandins in-vitro. Gao et al., J. Immunol. (2017); 199:2043-2054. In addition, multiple inflammatory signals (i.e., TNFα, IL6, CXCL10) have been reported to be attenuated by AMPION®, including a decrease in vascular permeability. Bar-Or et al., On the Mechanisms of Action of the Low Molecular Weight Fraction of Commercial Human Serum Albumin in Osteoarthritis. Current Rheumatology Reviews (2019), 15, 189-200.

Third, more than 1,000 patients with another inflammatory disease, osteoarthritis, have received AMPION® without any serious drug related adverse events. A subset of these patients were given AMPION® multiple times over the course of a year, and no serious drug related adverse events were observed.

Fourth, AMPION® is formulated as a sterile liquid and is easily administered as a nebulized liquid form or intravenously. AMPION®, particularly in aerosolized and/or nebulized form, can be used in the treatment of viral diseases and related conditions. For example, easing use for treatment of Acute Respiratory Distress Syndrome ("ARDS"), AMPION® is an aqueous solution that may be delivered through nebulization and would be suitable for suppressing inflammation in the lungs.

Physiologically-acceptable salts of the DA-DKP of the present disclosure may also be used in the practice of the present disclosure. Physiologically-acceptable salts include conventional non-toxic salts, such as salts derived from inorganic acids (such as hydrochloric, hydrobromic, sulfuric, phosphoric, nitric, and the like), organic acids (such as acetic, propionic, succinic, glycolic, stearic, lactic, malic, tartaric, citric, glutamic, aspartic, benzoic, salicylic, oxalic, ascorbic acid, and the like) or bases (such as the hydroxide, carbonate or bicarbonate of a pharmaceutically-acceptable metal cation or organic cations derived from N,N-dibenzylethylenediamine, D-glucosamine, or ethylenediamine). The salts are prepared in a conventional manner, e.g., by neutralizing the free base form of the compound with an acid.

Additional objects, advantages and novel features of the present disclosure will become apparent to those skilled in the art by consideration of the following non-limiting examples. The following experimental results are provided for purposes of illustration and are not intended to limit the scope of the claims.

EXAMPLES

Example 1. A Randomized, Controlled Study to Evaluate the Safety and Efficacy of AMPION® in Patients with Prolonged Respiratory Complications After COVID-19 Infection This study focuses on patients who have long-term symptoms and clinical signs related to continued respiratory illness after the viral infection is cleared.

AMPION® is delivered by inhalation using a nebulizer as a 32 cubic centimeters (cc) daily dose administered four times a day (8 cc per treatment) for five days, for a total dose of a total combined dose of 160 cc. This treatment regimen provides a positive clinical outcome while minimizing safety risks.

AMPION® is aerosolized for inhalation using the AEROGEN® Ultra handheld nebulizer (Aerogen Limited, Galway, Ireland, FDA 510K K133360), which consists of the AEROGEN® Pro-X Controller and the AEROGEN® Ultra handheld unit. The system is a portable medical device for single patient use indicated for aerosolization of physician-prescribed solutions for inhalation. AMPION® is nebulized using the continuous setting on the AEROGEN® controller, and the study drug is nebulized until it is fully aerosolized.

This is a randomized, controlled Phase 1 trial to evaluate the safety and efficacy of a 5-day AMPION® inhalation treatment in participants with prolonged respiratory complications after a COVID-19 infection. Participants (n=40) are randomized in active (n=20) or control (n=20) groups. Both groups receive the standard of care (SOC) for individuals with prolonged COVID-19 symptoms. The treatment arm receives AMPION® inhalation treatment in addition to the SOC, and the control arms will receive the SOC alone.

The trial objectives are to evaluate the safety and tolerability of inhaled AMPION® in adult participants with prolonged respiratory complications after COVID-19 infection and to assess the effect of inhaled AMPION® compared to SOC on the clinical outcomes for participants with prolonged respiratory complications after a COVID-19 infection. The effect of AMPION® compared to SOC on safety is determined by assessing incidence of adverse events (AEs) and serious adverse events (SAEs) from baseline through Day 28. The effect of AMPION® compared to SOC on respiratory symptom improvement is assessed by time to respiratory symptom improvement as measured using the symptom questionnaire from baseline through Day 7 and the percentage of participants demonstrating improvement on the respiratory symptom questionnaire on Days 1 through 7. The effect of AMPION® compared to SOC on respiratory symptom resolution is assessed by time to respiratory symptom resolution as described using the symptom questionnaire from baseline through Day 7 and change in the respiratory symptom questionnaire from baseline through Day 7. The effect of AMPION® compared to SOC on pulmonary function is assessed by change in blood oxygen saturation from baseline through Day 7, change in six-minute walk test score from baseline through Day 7, change in pulmonary function tests (spirometry, lung volume, diffusion capacity) from baseline through Day 7, and change in chest x-ray imaging from baseline to Day 28.

Diagnosis and Main Criteria for Inclusion:
1. Male or female adults: ≥18 years
2. Prior diagnosis with COVID-19, as evaluated by PCR test confirming infection, or suspected COVID-19 diagnosis based on radiological clinical findings.
3. Two negative COVID-19 tests to indicate infection has cleared.
4. Experiencing two or more COVD-19 respiratory symptoms for at least 4 weeks (28 days) after initial positive COVID-19 diagnosis, including cough, sore throat, stuffy or runny nose, shortness of breath (difficulty breathing), tightness of chest, chest discomfort, and low exercise tolerance
5. No clinical signs indicative of severe or critical COVID-19, including respiratory failure, shock, multi-organ failure.
6. No clinically significant findings via electrocardiogram (ECG), including acute myocardial infarction, acute ischemic changes, atrial fibrillation, atrial flutter, paced rhythms in individuals who have undergone permanent pacemaker placement, evidence of prior infarction, unchanged stable conduction abnormalities e.g., right bundle branch block, or any other finding which does not significantly impact mortality.
7. Women of childbearing potential and their partner must agree to use at least one highly effective method of contraception (e.g., hormonal contraceptives [implants, injectables, combination oral contraceptives, transdermal patches, or contraceptive rings], intrauterine devices, bilateral tubal occlusion, or sexual abstinence) for the duration of the study.
8. Informed consent obtained from the patient or the patient's legal representative.

Main Criteria for Exclusion:
1. Severe or critical COVID-19 with clinical diagnosis of respiratory failure, pneumonia, or acute respiratory distress syndrome (ARDS).
2. Patient has severe chronic obstructive or restrictive pulmonary disease (COPD) as defined by prior pulmonary function tests, chronic renal failure, or significant liver abnormality (e.g., cirrhosis, transplant, etc.).
3. Patient is on chronic immunosuppressive medication.
4. Patient requires surgery that could be life-threatening within the study window.
5. A history of allergic reactions to human albumin (reaction to non-human albumin such as egg albumin is not an exclusion criterion) or excipients in 5% human albumin (N-acetyltryptophan, sodium caprylate).
6. Patient has known pregnancy or is currently breastfeeding.
7. Participation in another clinical trial for an investigational treatment for COVID-19.
8. No clinically significant findings via electrocardiogram (ECG), including acute myocardial infarction, acute ischemic changes, atrial fibrillation, atrial flutter, paced rhythms in individuals who have undergone permanent pacemaker placement, evidence of prior infarction, unchanged stable conduction abnormalities e.g., right bundle branch block, or any other finding which does not significantly impact mortality.
9. As a result of the medical review and screening investigation, the Principal Investigator considers the patient unfit for the study.

Safety is assessed by recording adverse events, vital signs, blood oxygen saturation, and laboratory findings (biochemistry, hematology) for the duration of treatment and for the length of the study (28 days).

Efficacy is assessed by recording the effects of IV AMPION® compared to SOC on the clinical outcomes for participants with prolonged respiratory complications after a COVID-19 infection using the following clinical outcomes: blood oxygen saturation, COVID-19 respiratory symptom assessment, a walk test, pulmonary function tests (e.g., spirometry, lung volume, and diffusion capacity), and chest x-ray. Assessments for clinical outcomes are performed from baseline through Day 7.

Description of Study Visits

Screening (−3 Days to Day 0)
  Evaluate all inclusion and exclusion criteria to ensure that patients meet all inclusion criteria and none of the exclusion criteria.
  Confirm date of initial positive COVID-19 test. Confirm date(s) of two negative follow up COVID-19 tests.
  Medical history, pre-existing conditions, and comorbidities. Include the symptom onset date for COVID-19 symptoms.
  Obtain informed consent before the starting any study specific procedures, including COVID testing.

Baseline (Day 0)
  Confirm eligibility (review inclusion/exclusion criteria).
  Demographics (age, sex, race, height and weight).
  Randomize patient to study arm. If randomized to the active treatment arm, start treatment within 24 hours.
  Vital signs: heart rate, systolic and diastolic BP, body temperature, respiratory rate.
  $SpO_2$ and supplementation oxygen mode/flow rate, as applicable.
  Respiratory symptom assessment and walk test.
  Pulmonary function tests (PFTs): spirometry, lung volume, diffusion capacity.
  Chest x-ray imaging.
  Hematology, biochemistry tests.
  Concomitant medications/therapies.
  AEs.

Treatment Period (Day 1 to Day 5)
  Subjects enrolled in the active treatment arm will administer inhaled AMPION® through nebulization daily. These subjects will have a general health check conducted via telephone or text message on Days 1, 3, 5.
  Vital signs: heart rate, systolic and diastolic BP, body temperature, respiratory rate.
  $SpO_2$ and supplementation oxygen mode/flow rate, as applicable.
  Respiratory symptom assessment and walk test.
  PFTs: spirometry, lung volume, diffusion capacity.
  Concomitant medications/therapies.
  AEs.

Post Treatment Follow Up (Day 7)
  Vital signs: heart rate, systolic and diastolic BP, body temperature, respiratory rate.
  $SpO_2$ and supplementation oxygen mode/flow rate, as applicable.
  Respiratory symptom assessment and walk test.
  Pulmonary function tests (PFTs): spirometry, lung volume, diffusion capacity.

Hematology, biochemistry tests.
Concomitant medications/therapies.
AEs.
Post-Treatment Follow-Up (Day 28)
Vital signs: heart rate, systolic and diastolic BP, body temperature, respiratory rate.
$SpO_2$ and supplementation oxygen mode/flow rate, as applicable.
Respiratory symptom assessment and walk test.
Pulmonary function tests (PFTs): spirometry, lung volume, diffusion capacity.
Chest x-ray imaging.
Concomitant medications/therapies.
AEs.
Assessment Methods
Demographic Data: Demographic data are collected: age, gender, race, height and weight, comorbidities.
Health Check: A general health check is be conducted every other day during the treatment period for the AMPION® treatment group.
Vital Signs: Vital signs are collected daily during the treatment period and at follow-up visits as follows: heart rate (or pulse rate), systolic BP, diastolic BP, body temperature, respiratory rate.
Blood Oxygen Saturation ($SpO_2$): $SpO_2$ is collected daily during the treatment period and at follow-up visits using a pulse-oxygen measuring device.
Respiratory Symptom Assessment: The symptoms and the date experiencing symptoms are recorded at every visit from baseline to Day 7. The following symptoms are evaluated: cough, sore throat, stuffy or runny nose, shortness of breath (difficulty breathing), tightness of chest, chest discomfort, low exercise tolerance. Each symptom is rated as follows: 0 None, 1 Mild, 2
Moderate, or 3 Severe.
Walk Test: A six-minute walk test is recorded at every visit from baseline to Day 28.
1. Flat, straight corridor 30 m (100 feet) in length
2. Turnaround points marked with a cone
3. Patient should wear comfortable clothes and shoes
4. Patient rests in chair for at least 10 minutes prior to test (i.e., no warm-up period)
5. Heart rate and pulse oxygen saturation ($SpO_2$) should be monitored throughout the test
6. If the patient is using supplemental oxygen, record the flow rate and type of device
7. Have patient stand and rate baseline dyspnea and overall fatigue using Borg scale (Borg G A. Psychophysical bases of perceived exertion. Med Sci Sports Exerc 1982; 14:377).
8. Set lap counter to zero and timer to six minutes
9. Instruct the patient: Remember that the object is to walk AS FAR AS POSSIBLE for 6 minutes, but don't run or jog. Pivot briskly around the cone.
10. Standardized encouragement statements should be provided at one minute intervals, such as "You are doing well. You have _____ minutes to go" and "Keep up the good work. You have _____ minutes to go."
11. At the end of the test, mark the spot where the patient stopped on the floor
12. If using a pulse oximeter, measure the pulse rate and $SpO_2$ and record
13. After the test record the Borg dyspnea and fatigue levels
14. Ask, "What, if anything, kept you from walking farther?"
15. Calculate the distance walked and record American Thoracic Society. ATS statement: Guidelines for the six-minute walk test. Am J Respir Crit Care Med 2002; 166:111.

Holland A E, Spruit M A, Troosters T, et al. An official European Respiratory Society/American Thoracic Society technical standard: field walking tests in chronic respiratory disease. Eur Respir J 2014; 44:1428.

Pulmonary Function Tests (PFTs): PFTs are recorded at every visit from baseline to Day 7 or 28 using spirometry, lung volume, and diffusion capacity tests.

Chest X-Ray Imaging: Chest x-ray images are taken at baseline and Day 28. The standard chest examination consists of a PA (posterioranterior) and lateral chest x-ray. The films are read together. The PA exam is viewed as if the patient is standing in front of you with their right side on your left. The patient is facing towards the left on the lateral view.

Hematology: Hematology lab tests are collected at baseline and on Day 7. In the case of an abnormal lab result, continue to collect and test those samples to follow subject through resolution. The following hematology labs are tested: white cell count, red blood cell count, hemoglobin, hematocrit, mean cell volume (MCV), mean cell hemoglobin (MCH), mean cell hemoglobin concentration (MCHC), platelets, neutrophils, lymphocytes, monocytes, eosinophils, and basophils.

Serum Biochemistry: Biochemistry lab tests are collected at baseline and on Day 7. In the case of an abnormal lab result, continue to collect and test those samples to follow subject through resolution. The following biochemistry lab tests are tested: sodium, potassium, chloride, bicarbonate, urea, creatinine, glucose, total calcium, phosphate, ferritin, high-sensitivity C-reactive protein (hs-CRP), protein, albumin, globulins, total bilirubin, alkaline phosphatase (ALP), alanine aminotransferase (ALT), aspartate aminotransferase (AST) and lactate dehydrogenase (LDH).

Concomitant Medications: Concomitant medications are collected: prior (pre-hospitalization) concomitant medications, in-patient concomitant medications.

Adverse Events: Any documented adverse event, which is any undesired medical occurrence in a patient or clinical investigation patient receiving a pharmaceutical product which does not necessarily have a causal relationship with this treatment. These include but are not limited to the following: cardiac injury, arrhythmia, septic shock, liver dysfunction, acute kidney injury, and multi-organ failure.

Example 2. A Randomized, Double-Blinded, Placebo-Controlled Phase II Study to Evaluate the Safety and Efficacy of Inhaled AMPION® in Adults with Respiratory Distress Secondary Due to COVID-19

This is a phase II randomized controlled trial (RCT) to evaluate inhaled AMPION® for adults with respiratory distress due to COVID-19. AMPION® is an immunomodulatory therapy with anti-inflammatory effects potentially treating COVID-19 patients with respiratory complications who have a need for supplemental oxygen and breathing assistance. AMPION® targets and reduces the production of inflammatory cytokines induced by viruses, including SARS-CoV-2, and mitigates the severity of the disease in patients, such as those for whom ongoing inflammation is responsible for COVID-19 disease severity and the progression to respiratory distress.

The primary trial objective is to evaluate the effect of AMPION® on all-cause mortality in adult participants with respiratory distress due to COVID-19. The secondary trial objectives are to evaluate the safety and efficacy of inhaled AMPION® versus control in improving the clinical course and outcomes of participants with respiratory distress due to COVID-19.

The primary endpoint assesses the effect of AMPION® compared to placebo on all-cause mortality. All-cause mortality is measured as the percentage of participants with a successful outcome (life) or unsuccessful outcome (death) by Day 28.

Secondary endpoints assess the effect of inhaled AMPION® treatment compared to placebo on the clinical outcomes for participants with respiratory distress COVID-19. The effect of AMPION® compared to placebo on safety is assessed as incidence of adverse events (AEs) and serious adverse events (SAEs) from baseline at Day 5. The effect of AMPION® compared to placebo on hospital stay is assessed as hospital length of stay (LOS) from admission to discharge. The effect of AMPION® compared to placebo on oxygen use is assessed as duration of oxygen use, blood oxygen saturation, and oxygen flow rate from baseline through Day 5. The effect of AMPION® compared to placebo on progression to respiratory failure is assessed as proportion of participants who progress to respiratory failure (i.e., need for mechanical ventilation, ECMO, non-invasive ventilation) by Day 28. The effect of AMPION® compared to placebo on intensive care is assessed as percentage of participants who require Intensive Care Unit (ICU) admission by Day 28 and as ICU LOS from ICU admission to discharge. The effect of AMPION® compared to placebo on clinical improvement is assessed as change in ordinal scale from baseline through Day 5 and as change in ordinal scale from baseline to hospital discharge.

Exploratory endpoints assess the effect of inhaled AMPION® treatment compared to placebo on the clinical outcomes for participants with respiratory distress due to COVID-19. The effect of AMPION® compared to placebo on clinical health is assessed as change in NEWS2 score from baseline through Day 5 and as change in NEWS2 score from baseline to hospital discharge. The effect of AMPION® compared to placebo cytokine profile is assessed as modulation of cytokine levels from baseline to Day 5.

Inclusion Criteria—Patients should fulfill all the following inclusion criteria:
1. Male or female, ≥18 years old
2. Diagnosed with COVID-19, as evaluated by laboratory diagnostic test or diagnosis based on radiological clinical findings.
3. Respiratory distress as evidenced by at least two of the following:
   Radiographic infiltrates by imaging (chest x-ray, CT scan, etc.)
   Recording of $SpO_2 \leq 90\%$ or the patient is requiring oxygen to maintain an $SpO_2 \geq 90\%$.
   Requiring supplemental oxygen.
   Diagnosis of mild, moderate, or severe ARDS by Berlin definition.
4. Informed consent obtained from the patient or the patient's legal representative.

Exclusion Criteria—Patients fulfilling one or more of the following criteria may not be enrolled in the study:
1. As a result of the medical review and screening investigation, the Principal Investigator considers the patient unfit for the study and/or progression to death is imminent and inevitable irrespective of the provision of treatments.
2. Patient has severe chronic obstructive or restrictive pulmonary disease (COPD) (as defined by prior pulmonary function tests), chronic renal failure, or significant liver abnormality (e.g., cirrhosis, transplant, etc.).
3. Patient has chronic conditions requiring chemotherapy or immunosuppressive medication.
4. A history of allergic reactions to human albumin (reaction to non-human albumin such as egg albumin is not an exclusion criterion) or ingredients in 5% human albumin (N-acetyltryptophan, sodium caprylate).
5. Prolonged QT interval.
6. Patient has known pregnancy or is currently breastfeeding.
7. Patient planning to become pregnant, or father a child, during the treatment and follow-up period and/or is not willing to remain abstinent or use contraception.
8. Participation in another clinical trial (not including treatments for COVID-19 as approved by the FDA through expanded access, emergency, or compassionate use), or participation in a trial in the last 30 days.

Participants are randomized 1:1 to one of two groups, active (AMPION®) or control (placebo). Participants randomized to the active arm (n=100) will receive a daily dose (32 mL/day) of AMPION® inhaled via nebulizer delivered in four equally divided doses of 8 mL, every 6 hours. Participants randomized to the control arm (n=100) will receive a daily dose (32 mL/day) of placebo inhaled via nebulizer delivered in four equally divided doses of 8 mL, every 6 hours. Treatment is repeated for 5 days.

Nebulized study intervention (active or placebo) is delivered using the AEROGEN® Solo Nebulizer System with the AEROGEN® Solo Adaptor (FDA 510K K133360) manufactured by AEROGEN® Limited, Galway, Ireland. The AEROGEN® Solo Adaptor is a vibrating mesh nebulizer with a drug reservoir used in a hospital setting for delivery of respiratory therapy, including the hand-held AEROGEN® Ultra, NIV, and/or a mechanically ventilated circuit.

All participants receive the SOC for COVID-19 in a hospital setting as required based on disease severity, or as required for the course of hospital stay as follows:
   Oxygen administration to maintain oxygen saturation of 90% or greater, including the use of supplemental oxygen, NIV, and mechanical ventilation circuits.
   Nursing physical that may include review of neurological; pulmonary; cardiac; gastrointestinal; and urinary assessment at least daily during treatment.
   Vital monitoring (heart rate, blood pressure, temperature, respiratory rate, $SpO_2$) at least daily during treatment.
   Telemetry monitoring to evaluate heart rhythm and rate.
   Diet as tolerated to satisfy nutritional needs.
   Treatments for COVID-19 symptoms including antibiotics, cough suppressants/expectorants, anti-coagulants, fever reducers/pain killers, anti-nausea drugs, and/or bronchodilators.
   Treatments for COVID-19 as approved by the FDA including expanded access, emergency, or compassionate use (i.e., remdesivir, dexamethasone, convalescent plasma).
   Medications are recorded as concomitant medication, tabulated, and compared among groups.

Primary efficacy is assessed by recording the effects of AMPION® compared to placebo on mortality. Secondary endpoints will evaluate safety and other clinical outcomes of AMPION® compared to placebo on length of stay (LOS) in the hospital, oxygen use (including $SpO_2$ and flow rate), progression to respiratory failure (i.e., need for mechanical ventilation, ECMO, non-invasive ventilation), need for intensive care, ICU LOS, and ordinal scale for clinical improvement (8-point scale). Exploratory endpoints will evaluate safety and other clinical outcomes of AMPION® compared to placebo National Early Warning Score (NEWS) 2 score for the degree of illness of a patient) and modulation of cytokine levels.

Safety is assessed by recording adverse events, vital signs, blood oxygen saturation, and laboratory findings (biochemistry, hematology) for the duration of treatment and for the length of stay in the hospital (as applicable). Laboratory tests (biochemistry, hematology) are performed at baseline and every other day through treatment and through hospital stay unless an abnormal value is observed. In the case of an abnormal lab result, continue to collect and test those samples to follow subject through resolution.

Description of Study Visits

Screening (−3 Days to Day 0)
Evaluate all inclusion and exclusion criteria to ensure that patients meet all inclusion criteria and none of the exclusion criteria.
Medical history, pre-existing conditions, and comorbidities. Include the symptom onset date for COVID-19 symptoms and date of COVID-19 test.
Diphenhydramine, hydroxychloroquine, and azithromycin all prolong the cardiac QT interval, increasing risk of fatal cardiac arrhythmia. Therefore, severely-ill subjects receiving multiple drugs that prolong QT intervals are reviewed carefully by the P.I. on a case-by-case adjudication for benefit-risk ratio and close cardiovascular monitoring. Note, subjects who have baseline QT prolongation are excluded from this study.
Obtain informed consent before the starting any study specific procedures, including COVID testing.
Baseline (Day 0)
Confirm eligibility (review inclusion/exclusion criteria).
Randomize patient to study arm.
Demographics (age, sex, race, height and weight)
Concomitant medications/therapies
Vital signs: heart rate, systolic and diastolic BP, body temperature, respiratory rate.
SpO$_2$ and supplementation oxygen mode/flow rate
ECG monitoring (telemetry) or 12-lead ECG: record aberrant changes in waves/intervals
Hematology, biochemistry tests
Cytokine and chemokine assays
Ordinal scale and NEWS2 assessments
AEs
Treatment Period (Day 1 to Day 5)
Begin inhalation treatment of study intervention (active or placebo) within 6 hours of randomization.
Concomitant medications/therapies
Vital signs: heart rate, systolic and diastolic BP, body temperature, respiratory rate
SpO$_2$ and supplementation oxygen mode/flow rate
ECG monitoring (telemetry) or 12-lead ECG: record aberrant changes in waves/intervals—monitored as needed for patients who have abnormal readings or events requiring measurements.
Hematology, biochemistry tests—these tests are performed at baseline and every other day through treatment and through hospital stay unless an abnormal value is observed. In the case of an abnormal lab result, continue to collect and test those samples to follow subject through resolution.
Cytokine and chemokine assays—these tests are performed at baseline and at Day 5.
Ordinal scale and NEWS2 assessments
AEs
Hospitalization Period, as applicable (Day 6 through hospital discharge)
Concomitant medications/therapies
Vital signs: heart rate, systolic and diastolic BP, body temperature, respiratory rate
SpO$_2$ and supplementation oxygen mode/flow rate
ECG monitoring (telemetry) or 12-lead ECG: record aberrant changes in waves/intervals—monitored as needed for patients who have abnormal readings or events requiring measurements.
Hematology, biochemistry tests—these tests are performed at baseline and every other day through treatment and through hospital stay unless an abnormal value is observed. In the case of an abnormal lab result, continue to collect and test those samples to follow subject through resolution.
Cytokine and chemokine assays—these tests are performed at hospital discharge.
Ordinal scale and NEWS2 assessments
AEs
Post-Treatment Follow-Up (Days 28, 60)
Mortality
Concomitant medications/therapies
Hospital LOS
ICU LOS
Ordinal scale and NEWS2 assessments
AEs
Assessment Methods Demographic Data: Demographic data are collected from medical records: age, gender, race, height and weight, comorbidities.

Medical History: Medical history and pre-existing conditions are collected from medical records.

Concomitant Medications: Concomitant medications are collected from the medical records: prior (pre-hospitalization) concomitant medications, in-patient concomitant medications.

Mortality: All-cause mortality is recorded at hospital discharge, Days 28 and 60, as applicable. Cause of mortality is assessed and documented. All-cause mortality is calculated for the primary endpoint as the percentage of participants with a successful outcome (life) or unsuccessful outcome (death).

Length of Stay (LOS): Dates of hospitalization and ICU admission as well as discharge dates are recorded at hospital discharge, Days 28 and 60, as applicable. The hospital LOS and ICU
LOS are calculated as follows:
ICU admission: defined (in days) as the first study day when ICU status is changed to "yes" minus baseline date+1
Hospital LOS: is defined (in days) as the date of hospital discharge minus date of hospital admission+1
ICU LOS: defined (in days) as the date moved out of ICU minus first study date when ICU admission changed to "yes" +1

Oxygen Use: Oxygen use measured as blood oxygen saturation (SpO$_2$) and oxygen flow rate (liters per minute, 1 pm) are recorded at every visit from baseline to Day 5.

Intubation/Extubation: Date and time of intubation/extubation and days on ventilator are recorded at hospital discharge, Days 28 and 60, as applicable. Proportion of participants who progress to respiratory failure (i.e., need for mechanical ventilation, ECMO, non-invasive ventilation, or high-flow nasal cannula oxygen) are evaluated.

Vital Signs: Vital signs are collected daily during the treatment period and at follow-up visits from medical records as follows: heart rate (or pulse rate), systolic BP, diastolic BP, body temperature (° F. in the US, ° C. out of the US), respiratory rate.

Hematology: Hematology lab tests are collected from the medical records at baseline and every other day through treatment and hospital stay (as applicable) unless an abnormal value is observed. In the case of an abnormal lab result, continue to collect and test those samples to follow subject through resolution. The following hematology labs are tested: white cell count, red blood cell count, hemoglobin, hematocrit, mean cell volume (MCV), mean cell hemoglobin (MCH), mean cell hemoglobin concentration (MCHC), platelets, neutrophils, lymphocytes, monocytes, eosinophils, and basophils.

Serum Biochemistry: Biochemistry lab tests are collected from the medical records at baseline and every other day through treatment and hospital stay (as applicable) unless an abnormal value is observed. In the case of an abnormal lab result, continue to collect and test those samples to follow subject through resolution. The following biochemistry lab tests are tested: sodium, potassium, chloride, bicarbonate, urea, creatinine, glucose, total calcium, phosphate, ferritin, high-sensitivity C-reactive protein (hs-CRP), protein, albumin, globulins, total bilirubin, alkaline phosphatase (ALP), alanine aminotransferase (ALT), aspartate aminotransferase (AST) and lactate dehydrogenase (LDH).

Cytokine and Chemokine Assays: Cytokine and chemokine assay lab test results are collected and recorded before and after treatment (at baseline and again at Day 5 and at hospital discharge). A cytokine panel is tested to include, but not limited to: Tumor Necrosis Factor alpha (TNFα), interferon gamma (IFNγ), Interleukin 1 beta (IL-1β), interleukins (IL-6, IL-8, IL-10, IL-12). Data is reported for research purposes, and the sample is destroyed after data is collected.

Ordinal Scale for Clinical Improvement: The clinical status is recorded at every visit from baseline to Day 60 using the World Health Organization (WHO) "Ordinal Scale for Clinical Improvement". This 8-point ordinal scale was created to be responsive to the eligible patient population, intervention, and course of illness of COVID-19. The following scores are collected:
Score Descriptor
0 No clinical or virological evidence of infection
1 No limitation of activities
2 Limitation of activities
3 Hospitalized, no oxygen
4 Hospitalized, oxygen by mask or nasal prongs
5 Hospitalized, non-invasive ventilation or high-flow oxygen
6 Hospitalized, mechanical ventilation
7 Hospitalized, ventilation+additional organ support–pressors, RRT, ECMO
8 Death NEWS2 Score for Determining the Degree of Illness: The National Early Warning Score 2 (NEWS2) score, a well-known clinical risk score, is recorded at every visit from baseline to Day 60 using the vitals collected during the visit. The NEWS2 score is recommended by the National Institute for Health and Care Excellence ("NICE") for managing COVID-19 patients.

Adverse Events: Any documented adverse event, which is any undesired medical occurrence in a patient or clinical investigation patient receiving a pharmaceutical product which does not necessarily have a causal relationship with this treatment. These include but are not limited to the following: cardiac injury, arrhythmia, septic shock, liver dysfunction, acute kidney injury, and multi-organ failure.

Results 27 patients have been enrolled in the study. The mean age of patients is 67 years, with 63% male and 93% white patients. Dexamethasone was administered for nearly all subjects (n=23), and REMDESIVIR® was used in 10 subjects. All patients have completed their 5-day treatment window, with no serious safety observations to date.

The study indicates positive clinical outcomes due to AMPION® use in COVID-19 patients with respiratory distress. The all-cause mortality in COVID-19 patients was lower in the AMPION® treatment arm compared to control (7.7% AMPION®; 21.4% SOC; n=27). Following 5-day treatment, it was observed that subjects who received AMPION® may require less oxygen than SOC patients (average oxygen use at 5 liters per minute, LPM, for AMPION®; 9 LPM for SOC) with a greater proportion of AMPION®-treated subjects remaining stable, or decreasing the amount of required oxygen, compared to SOC (86% of AMPION®; 75% of SOC). Improvement on the WHO ordinal scale were observed in AMPION® patients as early as Day 2 and continued to Day 5 with 86% vs 75% of patients remaining stable or demonstrating improvement with AMPION® treatment compared to SOC, respectively, by Day 5. In subjects who have been discharged from the hospital (n=17), patients who received AMPION® required less hospitalization time overall compared to SOC alone (6 days with AMPION® treatment; 9 days with SOC).

Example 3. A Randomized, Double-Blinded, Placebo-Controlled Phase I/II Study to Evaluate the Safety and Efficacy of Intravenous AMPION® in Adult COVID-19 Patients Requiring Oxygen Supplementation There are primary endpoints for safety and efficacy. The primary endpoint for safety is incidence and severity of AEs at Day 5. The primary efficacy endpoint is the effect of AMPION® on all-cause mortality by Day 28.

Secondary efficacy endpoints assess the effect of IV AMPION® compared to SOC on the clinical outcomes for participants with COVID-19 who require supplemental oxygen. The effect of AMPION® compared to placebo on hospital stay is assessed as hospital length of stay (LOS) from admission to discharge. The effect of AMPION® compared to placebo on oxygen use is assessed as duration of oxygen use, blood oxygen saturation, and oxygen flow rate from baseline through Day 5. The effect of AMPION® compared to placebo on progression to respiratory failure is assessed as proportion of participants who progress to respiratory failure (i.e., need for mechanical ventilation, ECMO, non-invasive ventilation) by Day 28. The effect of AMPION® compared to placebo on intensive care is assessed as percentage of participants who require Intensive Care Unit (ICU) admission by Day 28 and as ICU LOS from ICU admission to discharge. The effect of AMPION® compared to placebo on clinical improvement is assessed as change in ordinal scale from baseline through Day 5 and as change in ordinal scale from baseline to hospital discharge. The effect of AMPION® compared to placebo on clinical health is assessed as change in NEWS2 score from baseline through Day 5 and as change in NEWS2 score from baseline to hospital discharge. The effect of AMPION® compared to placebo on oxygen use is assessed as duration of oxygen use, blood oxygen saturation, and oxygen flow rate from baseline through Day 5.

The participant population are those infected with SARS-CoV-2 that have developed severe symptoms consistent with COVID-19 and require supplemental oxygen to maintain blood oxygen saturation levels. Treatment of COVID-19 depends on the stage and severity of disease with a hyper-inflammatory state observed in the moderate to severe stages that are thought to lead to clinical complications, so treatment with immunomodulators at this point in the disease is more effective than anti-viral treatments.

Inclusion Criteria

Patients should fulfill all the following inclusion criteria:
1. Male or female, ≥18 years old.
2. Diagnosed with COVID-19, as evaluated by laboratory diagnostic test or diagnosis based on radiological clinical findings.
3. Clinical signs indicative of severe systemic illness with COVID-19, such as respiratory rate ≥30 per minute, heart rate ≥125 per minute, $SpO_2 \leq 93\%$ on room air at sea level ($SpO_2 \leq 90\%$ at altitude) or $PaO_2/FiO_2 \leq 300$
4. Patient is receiving supplemental oxygen to maintain a $SpO_2 \geq 90\%$.
5. Informed consent obtained from the patient or the patient's legal representative.

Exclusion Criteria

Patients fulfilling one or more of the following criteria may not be enrolled in the study:
1. As a result of the medical review and screening investigation, the Principal Investigator considers the patient unfit for the study and/or progression to death is imminent and inevitable irrespective of the provision of treatments.
2. Patient has severe chronic obstructive or restrictive pulmonary disease (COPD) (as defined by prior pulmonary function tests), chronic renal failure, or significant liver abnormality (e.g., cirrhosis, transplant, etc.).
3. Patient has chronic conditions requiring chemotherapy or immunosuppressive medication.
4. A history of allergic reactions to human albumin (reaction to non-human albumin such as egg albumin is not an exclusion criterion) or ingredients in 5% human albumin (N-acetyltryptophan, sodium caprylate).
5. Prolonged QT interval.
6. Patient has known pregnancy or is currently breastfeeding.
7. Patient planning to become pregnant, or father a child, during the treatment and follow-up period and/or is not willing to remain abstinent or use contraception.
8. Participation in another clinical trial (not including treatments for COVID-19 as approved by the FDA through expanded access, emergency, or compassionate use), or participation in a trial in the last 30 days.

Study Plan

Participants randomized to the active arm (n=30) receive a daily dose (250 mL/day) of IV AMPION® delivered in two equally divided doses of 125 mL, every 12 hours. Participants randomized to the control arm (n=30) receive a daily dose (250 mL/day) of IV placebo delivered in two equally divided doses of 125 mL, every 12 hours. Treatment is repeated for 5 days.

Intravenous study intervention (active or placebo) AMPION® are administered using an infusion pump through an existing intravenous access (central line, PICC, peripheral, or saline lock). AMPION® is administered as an intravenous piggyback/secondary if the patient at the time of the administration of AMPION® has an existing primary infusion. If there are no intravenous fluids being administered at the time of the AMPION® infusion, AMPION® treatment is infused as an intermittent intravenous infusion. AMPION® is administered undiluted at a flow rate of 100 cc/hour.

All participants receive the SOC for COVID-19 in a hospital setting as required based on disease severity, or as required for the course of hospital stay as follows:
  Oxygen administration to maintain oxygen saturation of 90% or greater.
  Nursing physical that may include review of neurological; pulmonary; cardiac; gastrointestinal; and urinary assessment at least daily during treatment.
  Vital monitoring (heart rate, blood pressure, temperature, respiratory rate, $SpO_2$) at least daily during treatment.
  Telemetry monitoring to evaluate heart rhythm and rate.
  Diet as tolerated to satisfy nutritional needs.
  Treatments for COVID-19 symptoms including antibiotics, cough suppressants/expectorants, anti-coagulants, fever reducers/pain killers, anti-nausea drugs, and/or bronchodilators.
  Treatments for COVID-19 as approved by the FDA including expanded access, emergency, or compassionate use (i.e., remdesivir, dexamethasone, convalescent plasma).
  Medications are recorded as concomitant medication, tabulated, and compared among groups.

Safety is assessed by recording adverse events, vital signs, blood oxygen saturation, and laboratory findings (biochemistry, hematology) for the duration of treatment and for the length of stay in the hospital (as applicable). Laboratory tests (biochemistry, hematology) are performed at baseline and every other day through treatment and through hospital stay unless an abnormal value is observed. In the case of an abnormal lab result, continue to collect and test those samples to follow subject through resolution.

Efficacy is assessed by recording the effects of IV AMPION® compared to placebo on the clinical outcomes for participants with COVID-19 using the following: mortality, oxygen use (including $SpO_2$ and flow rate), need for intensive care, length of stay (LOS) in the hospital, LOS in the ICU, ordinal scale for clinical improvement (8-point scale), National Early Warning Score (NEWS) 2 score for the degree of illness of a patient, and modulation of cytokine levels.

Description of Study Visits
  Screening (−3 Days to Day 0)
    Evaluate all inclusion and exclusion criteria to ensure that patients meet all inclusion criteria and none of the exclusion criteria.
    Medical history, pre-existing conditions, and comorbidities. Include the symptom onset date for COVID-19 symptoms and date of COVID-19 test.
    Diphenhydramine, hydroxychloroquine, and azithromycin all prolong the cardiac QT interval, increasing risk of fatal cardiac arrhythmia. Therefore, severely-ill subjects receiving multiple drugs that prolong QT intervals are reviewed carefully by the P.I. on a case-by-case adjudication for benefit-risk ratio and close cardiovascular monitoring. Note, subjects who have baseline QT prolongation are excluded from this study.
    Obtain informed consent before the starting any study specific procedures, including COVID testing.
  Baseline (Day 0)
    Confirm eligibility (review inclusion/exclusion criteria).
    Randomize patient to study arm.
    Demographics (age, sex, race, height and weight)

Concomitant medications/therapies
Vital signs: heart rate, systolic and diastolic BP, body temperature, respiratory rate
SpO$_2$ and supplementation oxygen mode/flow rate
ECG monitoring (telemetry) or 12-lead ECG: record aberrant changes in waves/intervals
Hematology, biochemistry tests
Cytokine and chemokine assays
Ordinal scale and NEWS2 assessments
AEs
Treatment Period (Day 1 to Day 5)
Administer AMPION® or placebo control as a daily IV infusion. Begin treatment within 6 hours of randomization.
Concomitant medications/therapies
Vital signs: heart rate, systolic and diastolic BP, body temperature, respiratory rate—vital signs are collected shortly after (within 30 minutes) treatment.
SpO$_2$ and supplementation oxygen mode/flow rate
ECG monitoring (telemetry) or 12-lead ECG: record aberrant changes in waves/intervals—monitored as needed for patients who have abnormal readings or events requiring measurements.
Hematology, biochemistry tests—these tests are performed at baseline and every other day through treatment and through hospital stay unless an abnormal value is observed. In the case of an abnormal lab result, continue to collect and test those samples to follow subject through resolution.
Cytokine and chemokine assays—these tests are performed at baseline and at Day 5.
Ordinal and NEWS2 assessments
AEs
Hospitalization Period, as applicable (Day 6 through hospital discharge)
Concomitant medications/therapies
Vital signs: heart rate, systolic and diastolic BP, body temperature, respiratory rate
SpO$_2$ and supplementation oxygen mode/flow rate
ECG monitoring (telemetry) or 12-lead ECG: record aberrant changes in waves/intervals—monitored as needed for patients who have abnormal readings or events requiring measurements.
Hematology, biochemistry tests—these tests are performed at baseline and every other day through treatment and through hospital stay unless an abnormal value is observed. In the case of an abnormal lab result, continue to collect and test those samples to follow subject through resolution.
Cytokine and chemokine assays—these tests are performed at hospital discharge.
Ordinal scale and NEWS2 assessments
AEs
Post-Treatment Follow-Up (Days 28, 60)
Mortality
Concomitant medications/therapies
Hospital LOS
ICU LOS
Ordinal scale and NEWS2 assessments
AEs
Assessment Methods
Demographic Data: Demographic data is collected from medical records: age, gender, race, height and weight, comorbidities.
Medical History: Medical history and pre-existing conditions are collected from medical records.
Concomitant Medications: Concomitant medications are collected from the medical records: prior (pre-hospitalization) concomitant medications, in-patient concomitant medications.
Mortality: All-cause mortality is recorded at hospital discharge, Days 28 and 60, as applicable. Cause of mortality is assessed and documented. All-cause mortality is calculated for the primary endpoint as the percentage of participants with a successful outcome (life) or unsuccessful outcome (death).
Length of Stay (LOS): Dates of hospitalization and ICU admission as well as discharge dates are recorded at hospital discharge, Days 28 and 60, as applicable. The hospital LOS and ICU LOS are calculated as follows:
ICU admission: defined (in days) as the first study day when ICU status is changed to "yes" minus baseline date+1
Hospital LOS: is defined (in days) as the date of hospital discharge minus date of hospital admission+1
ICU LOS: defined (in days) as the date moved out of ICU minus first study date when ICU admission changed to "yes" +1
Oxygen Use: Oxygen use measured as blood oxygen saturation (SpO$_2$) and oxygen flow rate (liters per minute, 1 pm) are recorded at every visit from baseline to Day 5.
Intubation/Extubation: Date and time of intubation/extubation and days on ventilator are recorded at hospital discharge, Days 28 and 60, as applicable. Proportion of participants who progress to respiratory failure (i.e., need for mechanical ventilation, ECMO, non-invasive ventilation, or high-flow nasal cannula oxygen) is evaluated.
Vital Signs: Vital signs are collected daily during the treatment period and at follow-up visits from medical records as follows: heart rate (or pulse rate), systolic BP, diastolic BP, body temperature (° F. in the US, ° C. out of the US), respiratory rate. Vital signs are collected shortly after (within 30 minutes) treatment.
Hematology: Hematology lab tests are collected from the medical records at baseline and every other day through treatment and hospital stay (as applicable) unless an abnormal value is observed. In the case of an abnormal lab result, continue to collect and test those samples to follow subject through resolution. The following hematology labs are tested: white cell count, red blood cell count, hemoglobin, hematocrit, mean cell volume (MCV), mean cell hemoglobin (MCH), mean cell hemoglobin concentration (MCHC), platelets, neutrophils, lymphocytes, monocytes, eosinophils, and basophils.
Serum Biochemistry: Biochemistry lab tests are collected from the medical records at baseline and every other day through treatment and hospital stay (as applicable) unless an abnormal value is observed. In the case of an abnormal lab result, continue to collect and test those samples to follow subject through resolution. The following biochemistry lab tests are tested: sodium, potassium, chloride, bicarbonate, urea, creatinine, glucose, total calcium, phosphate, ferritin, high-sensitivity C-reactive protein (hs-CRP), protein, albumin, globulins, total bilirubin, alkaline phosphatase (ALP), alanine aminotransferase (ALT), aspartate aminotransferase (AST) and lactate dehydrogenase (LDH).
Cytokine and Chemokine Assays: Cytokine and chemokine assay lab test results are collected and recorded before and after treatment (at baseline and again at Day 5 and at hospital discharge). A cytokine panel is tested to include, but not limited to: Tumor Necrosis Factor alpha (TNFα), interferon gamma (IFNγ), Interleukin 1 beta (IL-1β), interleukins (IL-6, IL-8, IL-10, IL-12). Data is reported for research purposes, and the sample is destroyed after data is collected.

Ordinal Scale for Clinical Improvement: The clinical status is recorded at every visit from baseline to Day 60 using the World Health Organization (WHO) "Ordinal Scale for Clinical Improvement". See Example 2 at Ordinal Scale for Clinical Improvement for further information on the ordinal scale.

NEWS2 Score for Determining the Degree of Illness: The National Early Warning Score 2 (NEWS2) score, a well-known clinical risk score, is recorded at every visit from baseline to Day 60 using the vitals collected during the visit. The NEWS2 score is recommended by the National Institute for Health and Care Excellence ("NICE") for managing COVID-19 patients.

Adverse Events: Any documented adverse event, which includes any undesired medical occurrence in a patient or clinical investigation patient receiving a pharmaceutical product which does not necessarily have a causal relationship with this treatment. These include but are not limited to the following: cardiac injury, arrhythmia, septic shock, liver dysfunction, acute kidney injury, and multi-organ failure.

Results

The incidence of adverse events (AEs) at day 90 was determined, which was successfully achieved with no treatment-related serious adverse events reported, and no difference in the incidence or severity of AEs between the AMPION® treatment and standard of care (SOC) at Day 5 and at the 90-day follow-up.

Ten hospitalized patients with lab-confirmed COVID-19 infection who were receiving supplemental oxygen were randomized 1:1 to AMPION® plus SOC (active) or SOC alone (control). The standard of care (SOC) included respiratory support, corticosteroids, and anti-viral therapies such as Remdesivir. The majority of patients were male (70%), white (90%), and had a median age of 74 years.

Nearly all (90%) patients received dexamethasone: 80% AMPION® and 100% SOC. Remdesivir was not required for AMPION® treated patients (0% AMPION® vs. 80% SOC). A greater proportion of patients treated with AMPION® had clinical improvement from baseline on the WHO ordinal scale on each day on treatment; Day 5 improvement was 75% AMPION® vs. 50% SOC. Likewise, a greater proportion of patients treated with AMPION® had improvements in oxygen requirements from baseline each day on treatment compared to SOC (Day 5 improvement: 75% AMPION® vs. 50% SOC).

Example 4. Calculation of AMPION® Dose

This example describes a method to calculate the dose of AMPION® for intravenous administration. This method can be applied to other administration routes.

Human serum albumin, including 5% human serum albumin (HSA), has been administered safely via IV for many years at volumes exceeding 500 cc in a day (5% HSA prescribing information). A comparison of the active components in AMPION® against those in the starting material HSA demonstrates that the proposed daily dose (250 cc) of AMPION® can be safely administered via IV.

A daily dose of 250 cc is based on AMPION®'s in vitro biological activity and the amount of AMPION® required to achieve its in vitro anti-inflammatory effect (FIG. 1). The biological activity of AMPION® was measured using a bioassay which tests the release of pro-inflammatory cytokine (TNFα) in activated immune cells. In the bioassay, human peripheral blood mononuclear cells (PBMC) are stimulated to release TNFα. The cells are treated with either AMPION® or saline, and AMPION® activity is reported as inhibition (%) of TNFα in cells treated with AMPION® compared to the cells treated with saline. In the bioassay, the treatment effect is achieved by adding 50 μL of AMPION® to 100,000 cells. A dose-dependent effect is observed.

To model efficacy of an in vivo clinical dose of AMPION®, the number blood monocytes in the bloodstream provides a means of estimating the concentration of immune cells in circulation. Based on the average monocyte density in an adult human bloodstream, and the ratio of cells used in the AMPION® TNFα bioassay, a therapeutic dose range of AMPION® (250-1187 cc) would be required to achieve the anti-inflammatory effect.

While various embodiments of the present disclosure have been described in detail, it is apparent that modifications and adaptations of those embodiments will occur to those skilled in the art. It is to be expressly understood, however, that such modifications and adaptations are within the scope of the present disclosure, as set forth in the following exemplary claims.

What is claimed:

1. A method of treating one or more symptoms of a SARS-Coronavirus-2 (SARS-CoV-2) infection in a patient, comprising administering to the patient a pharmaceutical composition comprising DA-DKP, wherein:
the pharmaceutical composition is prepared by fractionating blood to produce a human serum albumin composition and removing components above 5 kDa from the human serum albumin composition.

2. The method of claim 1, wherein the one or more symptoms are selected from the group consisting of acute respiratory distress syndrome (ARDS), acute lung injury (ALI), interstitial lung disease, pulmonary fibrosis, pneumonia, reactive airway disease syndrome, respiratory distress requiring supplemental oxygen, long COVID and combinations thereof.

3. The method of claim 1, wherein the one or more symptoms are selected from the group consisting of fatigue, shortness of breath or difficulty breathing, low exercise tolerance, low blood oxygen saturation, cough, sore throat, stuffy or runny nose, joint pain, chest pain, tightness or discomfort, muscle pain, muscle weakness, fever, heart palpitations, difficulty thinking and/or concentrating, depression and combinations thereof.

4. The method of claim 3, wherein the patient has experienced the one or more symptoms for at least four weeks, at least one month, at least two months, or at least three months.

5. The method of claim 1, wherein the administration results in an outcome selected from the group consisting of reduced ventilator time, reduced mortality, improvement in oxygenation parameters, reduced time to resolution of one or more respiratory symptoms, improved pulmonary function, and combinations thereof.

6. The method of claim 1, wherein, after the administration, the patient achieves improvement on the World Health Organization COVID-19 ordinal scale of at least 4, at least 3, at least 2, or at least 1.

7. The method of claim 1, wherein the composition is administered in a form suitable for administration to the lungs.

8. The method of claim 7, wherein the composition is administered in a nebulized form at a dose of 8 milliliters, quater in die, for five days.

9. The method of claim 1, wherein the composition further comprises N-acetyl-tryptophan (NAT), caprylic acid, caprylate or combinations thereof.

10. A method of treating inflammation associated with a SARS-Coronavirus-2 (SARS-CoV-2) infection in a patient, comprising administering to the patient a pharmaceutical composition comprising DA-DKP, wherein:
   the pharmaceutical composition is prepared by fractionating blood to produce a human serum albumin composition and removing components above 5 kDa from the human serum albumin composition.

11. The method of claim 10, wherein the inflammation is of a tissue selected from the group consisting of lung, brain, heart, kidney, blood vessel, skin, nerve, and combinations thereof.

12. The method of claim 10, wherein the inflammation causes a symptom selected from the group consisting of fatigue, shortness of breath or difficulty breathing, low exercise tolerance, low blood oxygen saturation, cough, sore throat, stuffy or runny nose, joint pain, chest pain tightness or discomfort, muscle pain, muscle weakness, fever, heart palpitations, difficulty thinking and/or concentrating, depression, and combinations thereof.

13. The method of claim 12, wherein the patient has experienced the symptom for at least four weeks, at least one month, at least two months, or at least three months.

14. The method of claim 10, wherein administration results in an outcome selected from the group consisting of reduced ventilator time, reduced mortality, improvement in oxygenation parameters, reduced time to resolution of one or more respiratory symptoms, improved pulmonary function, and combinations thereof.

15. The method of claim 10, wherein, after the administration, the patient achieves improvement on the World Health Organization COVID-19 ordinal scale of at least 4, at least 3, at least 2, or at least 1.

16. The method of claim 10, wherein the patient has or had respiratory distress requiring supplemental oxygen caused by SARS-Coronavirus-2 (SARS-CoV-2) infection.

17. The method of claim 10, wherein the composition is administered in a form suitable for administration to the lungs.

18. The method of claim 17, wherein the composition is administered in a nebulized form at a dose of 8 milliliters quater in die for five days.

* * * * *